US009307995B2

(12) United States Patent
Paul et al.

(10) Patent No.: US 9,307,995 B2
(45) Date of Patent: Apr. 12, 2016

(54) METHODS, SYSTEMS AND DEVICES FOR THE DELIVERY OF ENDOLUMINAL PROSTHESES

(75) Inventors: Ram H. Paul, Bloomington, IN (US);
Brian C. Case, Lake Villa, IL (US);
Jacob A. Flagle, New Palestine, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1864 days.

(21) Appl. No.: 11/763,773

(22) Filed: Jun. 15, 2007

(65) Prior Publication Data

US 2007/0292472 A1 Dec. 20, 2007

Related U.S. Application Data

(60) Provisional application No. 60/813,853, filed on Jun. 15, 2006.

(51) Int. Cl.
*A61B 17/08* (2006.01)
*A61B 17/12* (2006.01)
(Continued)

(52) U.S. Cl.
CPC ....... *A61B 17/12022* (2013.01); *A61B 17/1219* (2013.01); *A61B 17/12109* (2013.01); *A61B 17/12181* (2013.01); *A61B 2017/00778* (2013.01); *A61B 2017/00867* (2013.01);
(Continued)

(58) Field of Classification Search
CPC ..................... A61B 17/12109; A61B 17/1219; A61B 17/12159; A61B 17/00637
USPC .................. 606/213, 200, 158; 623/1.23
See application file for complete search history.

(56) References Cited

U.S. PATENT DOCUMENTS 4,511,653 A 4/1985 Play et al.
4,512,342 A 4/1985 Zaneveld et al.
(Continued)

FOREIGN PATENT DOCUMENTS

EP 0711532 5/1996
WO WO 87/00062 1/1987
(Continued)

OTHER PUBLICATIONS

Heeschen, C., et al. "Nicotine Stimulates Angiogenesis and Promotes Tumor Growth and Atherosclerosis". Nature Medicine, vol. 7., No. 7, Jul. 2001. pp. 833-839.
(Continued)

*Primary Examiner* — Alexander Orkin
(74) *Attorney, Agent, or Firm* — Woodard, Emhardt, Moriarty, McNett & Henry LLP

(57) ABSTRACT

Described are devices, methods, and systems for achieving occlusion of vascular vessels. Further described are certain reduced or low profile procedures and devices for the percutaneous occlusion of the saphenous vein, such as in the treatment of a varicose vein condition caused by venous reflux. Devices and procedures can involve an endoluminal delivery device having an atraumatic distal end, that is advancable through a vascular vessel, and an occlusion device received on the endoluminal delivery device. The endoluminal delivery device can have one or more adaptations for releasably receiving the occlusion device. The occlusion device can include a sponge form material. The occlusion device can include a remodelable material or a synthetic material. The occlusion device can include an anchor.

50 Claims, 11 Drawing Sheets

(51) Int. Cl.
*A61B 17/00* (2006.01)
*A61B 17/22* (2006.01)

(52) U.S. Cl.
CPC .............. *A61B2017/00898* (2013.01); *A61B 2017/1205* (2013.01); *A61B 2017/22038* (2013.01)

(56) References Cited

U.S. PATENT DOCUMENTS

| | | |
|---|---|---|
| 4,705,517 A | 11/1987 | DiPisa, Jr. |
| 4,819,637 A | 4/1989 | Dormandy, Jr. et al. |
| 4,902,508 A | 2/1990 | Badylak et al. |
| 4,956,178 A | 9/1990 | Badylak et al. |
| 5,192,301 A * | 3/1993 | Kamiya et al. ............... 606/213 |
| 5,192,302 A | 3/1993 | Kensey et al. |
| 5,217,484 A | 6/1993 | Marks |
| 5,222,970 A | 6/1993 | Reeves |
| 5,281,422 A | 1/1994 | Badylak et al. |
| 5,292,332 A * | 3/1994 | Lee ............................... 606/213 |
| 5,304,123 A | 4/1994 | Atala et al. |
| 5,312,415 A | 5/1994 | Palermo |
| 5,334,210 A | 8/1994 | Gianturco |
| 5,370,660 A * | 12/1994 | Weinstein et al. ............. 606/215 |
| 5,382,261 A | 1/1995 | Palmaz |
| 5,411,475 A | 5/1995 | Atala et al. |
| 5,437,631 A * | 8/1995 | Janzen ........................... 604/506 |
| 5,443,478 A | 8/1995 | Purdy |
| 5,456,693 A | 10/1995 | Conston et al. |
| 5,514,158 A * | 5/1996 | Kanesaka ...................... 606/213 |
| 5,554,389 A | 9/1996 | Badylak et al. |
| 5,571,181 A | 11/1996 | Li |
| 5,611,358 A | 3/1997 | Suval |
| 5,656,036 A | 8/1997 | Palmaz |
| 5,676,962 A | 10/1997 | Cabrera Garrido et al. |
| 5,720,764 A * | 2/1998 | Naderlinger .................. 606/200 |
| 5,725,552 A * | 3/1998 | Kotula et al. ................. 606/213 |
| 5,779,672 A | 7/1998 | Dormandy |
| 5,830,228 A | 11/1998 | Knapp et al. |
| 5,925,062 A | 7/1999 | Purdy |
| 5,925,063 A | 7/1999 | Khosravi |
| 5,955,110 A | 9/1999 | Patel et al. |
| 5,993,844 A | 11/1999 | Abraham et al. |
| 6,096,052 A | 8/2000 | Callister et al. |
| 6,099,567 A | 8/2000 | Badylak et al. |
| 6,126,686 A | 10/2000 | Badylak et al. |
| 6,174,322 B1 | 1/2001 | Schneidt |
| 6,206,907 B1 | 3/2001 | Marino et al. |
| 6,206,931 B1 | 3/2001 | Cook et al. |
| 6,221,091 B1 | 4/2001 | Khosravi |
| 6,245,090 B1 | 6/2001 | Gilson et al. |
| 6,254,608 B1 | 7/2001 | Solar |
| 6,258,120 B1 * | 7/2001 | McKenzie et al. ........... 623/1.36 |
| 6,299,619 B1 | 10/2001 | Greene, Jr. et al. |
| 6,344,041 B1 | 2/2002 | Kupiecki et al. |
| 6,375,989 B1 | 4/2002 | Badylak et al. |
| 6,379,368 B1 | 4/2002 | Corcoran et al. |
| 6,432,116 B1 | 8/2002 | Callister et al. |
| 6,547,804 B2 | 4/2003 | Porter et al. |
| 6,572,873 B1 | 6/2003 | Osman et al. |
| 6,589,256 B2 | 7/2003 | Forber |
| 6,592,566 B2 | 7/2003 | Kipke et al. |
| 6,638,293 B1 * | 10/2003 | Makower et al. .............. 606/200 |
| 6,645,167 B1 | 11/2003 | Whalen, II et al. |
| 6,746,426 B1 | 6/2004 | Flaherty et al. |
| 6,790,220 B2 | 9/2004 | Morris et al. |
| 7,744,621 B2 * | 6/2010 | Paul et al. ..................... 606/195 |
| 2001/0041900 A1 | 11/2001 | Callister et al. |
| 2002/0010418 A1 | 1/2002 | Lary et al. |
| 2002/0058640 A1 | 5/2002 | Abrams et al. |
| 2002/0168366 A1 | 11/2002 | Stewart et al. |
| 2002/0188319 A1 * | 12/2002 | Morris et al. ................. 606/213 |
| 2003/0013989 A1 | 1/2003 | Obermiller et al. |
| 2003/0051735 A1 | 3/2003 | Pavcnik et al. |
| 2003/0059372 A1 | 3/2003 | Whalen et al. |
| 2003/0082224 A1 | 5/2003 | Noujaim et al. |
| 2003/0120256 A1 | 6/2003 | Lary et al. |
| 2003/0153935 A1 | 8/2003 | Mialhe |
| 2003/0229366 A1 | 12/2003 | Reggie et al. |
| 2004/0044351 A1 | 3/2004 | Searle |
| 2004/0087930 A1 | 5/2004 | Whalen et al. |
| 2004/0087998 A1 | 5/2004 | Lee et al. |
| 2004/0093007 A1 | 5/2004 | Sussman et al. |
| 2004/0097901 A1 | 5/2004 | Whalen et al. |
| 2004/0143288 A1 | 7/2004 | Searle |
| 2004/0210211 A1 | 10/2004 | Devens, Jr. et al. |
| 2004/0210249 A1 | 10/2004 | Fogarty |
| 2005/0085842 A1 * | 4/2005 | Eversull et al. ............... 606/191 |
| 2005/0113737 A1 * | 5/2005 | Ashby et al. .................... 604/15 |
| 2005/0154454 A1 * | 7/2005 | Hunter et al. ................ 623/1.42 |
| 2005/0155608 A1 | 7/2005 | Pavcnik et al. |
| 2005/0267527 A1 * | 12/2005 | Sandoval et al. ............. 606/213 |
| 2006/0212055 A1 * | 9/2006 | Karabey et al. ............... 606/158 |

FOREIGN PATENT DOCUMENTS

| | | |
|---|---|---|
| WO | WO 94/26175 | 11/1994 |
| WO | WO 97/19643 | 6/1997 |
| WO | WO 98/22158 | 5/1998 |
| WO | WO 98/25545 | 6/1998 |
| WO | WO 98/25637 | 6/1998 |
| WO | WO 00/32112 | 6/2000 |
| WO | WO 00/32250 | 6/2000 |
| WO | WO 00/32253 | 6/2000 |
| WO | WO 2005/020847 | 3/2005 |
| WO | WO 2005/053547 | 6/2005 |
| WO | WO 2005/053547 A2 | 6/2005 |

OTHER PUBLICATIONS

Johnson, C., et al. "Matrix Metalloproteinase-9 is Required for Adequate Angiogenic Revascularization of Ischemic Tissues: Potential Role in Capillary Branching". Circulation Research, vol. 94. (2004) pp. 262-268.

PCT International Search Report, PCT/US2007/071360, 5 pages.

PCT Written Opinion, PCT/US2007/071360, 9 pages.

* cited by examiner

METHODS, SYSTEMS AND DEVICES FOR THE DELIVERY OF ENDOLUMINAL PROSTHESES

REFERENCE TO RELATED APPLICATION

The present application claims the benefit of U.S. Provisional Patent Application Ser. No. 60/813,853 filed Jun. 15, 2006 entitled "Methods, Systems, and Devices for the Delivery of Endoluminal Prostheses" which is hereby incorporated by reference in its entirety.

BACKGROUND

The present invention resides generally in the field of devices and methods useful for the deployment of prosthetic devices, and in a particular aspect relates to the deployment of prosthetic devices within the vasculature of a patient to treat complications, such as a varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of one or more sclerosing agents to the lumen of a varicose or other small diameter vein, which induce the vein to collapse and the venous walls to fuse, thereby closing the vein.

In view of this background, the need remains for improved and alternative techniques, devices and systems for affecting the venous system to treat venous conditions. The present invention is addressed to these needs.

SUMMARY OF THE INVENTION

Accordingly, in one aspect, the present invention provides a device that is advancable through a bodily vessel and configured to carry and release an occlusion device within the vessel to cause closure of the vessel. The device may include an adaptation configured to releasably retain the occlusion device during the deployment procedure. In additional aspects, the present invention provides an implantable occlusive device configured for advancement through a venous vessel so as to become deployed and implanted within the vessel to cause closure thereof.

In another aspect, the present invention provides a medical product for closing a vascular vessel of a patient that includes an endoluminal delivery device and an occlusion device. The endoluminal delivery device has an atraumatic distal end and is advancable through a vascular vessel. The occlusion device is releasably received on the endoluminal delivery device.

In yet another aspect, the present invention provides a medical product for delivering an occlusive device that includes an endoluminal delivery device. The delivery device has one or more adaptations that are configured to contact an occlusive device during a deployment procedure so as to maintain the position of the occluder during delivery yet release the occluder after delivery. The delivery device is configured to deploy the occlusive device to occlude a bodily lumen of a patient.

In still yet another aspect, the present invention provides a medical product for closing a vascular vessel of a patient that includes an atraumatic elongate guiding member that is receivable within a patient's vascular vessel and an occlusion device that is configured for receipt over the guiding member.

In another aspect, the present invention provides a method for occluding a vascular vessel that includes providing an occlusive device that is releasably retained on an endoluminal delivery device. The method involves locating the occlusive device and the endoluminal device at a site within a vascular vessel and thereafter releasing the occlusive device in proximity to the vascular site so as to occlude or close the vascular vessel.

In yet another aspect, the present invention provides a method for the delivery of an endoluminal device that includes providing an elongate guiding member that has an atraumatic tip and is receivable within a venous vessel. Also provided is a sponge form occlusion device that is configured for slidable receipt over the elongate guiding member. The method includes percutaneously locating the elongate guiding member and the sponge form occlusion device within a venous vessel and thereafter removing the elongate guiding member from the venous vessel so as to implant the occlusion device within the vessel.

In still yet another aspect, the present invention provides a medical kit that includes a medical product as disclosed herein enclosed in sterile medical packaging.

In another aspect, the present invention provides a medical product for occluding the saphenous vein. The medical device includes an elongate implantable occlusion device that comprises an extracellular matrix material and has sufficient column strength for advancement through a saphenous vein.

The present invention provides improved and/or alternative methods, systems, and devices for deploying vascular prostheses or other prostheses within other bodily vessels. Additional embodiments as well as features and advantages of the invention will be apparent from the further descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the present invention provide methods, devices, and systems for occluding vascular vessels in the treatment of certain vascular deficiencies, such as those involved in venous valve insufficiency (VVI). More particularly, the present invention provides reduced profile devices for delivering and implanting occlusion devices within certain venous vessels, such as the greater saphenous vein (GSV). For example, in one aspect, the present invention provides a device that is advancable through a bodily vessel and configured to carry and release an occlusion device within the vessel to cause closure of the vessel. The device may include one or more adaptations configured to releasably retain the occlusion device during the deployment procedure. In additional aspects, the present invention provides an implantable occlusive device configured for advancement through a venous vessel so as to become deployed and implanted within the vessel to cause closure thereof.

Figure 1:
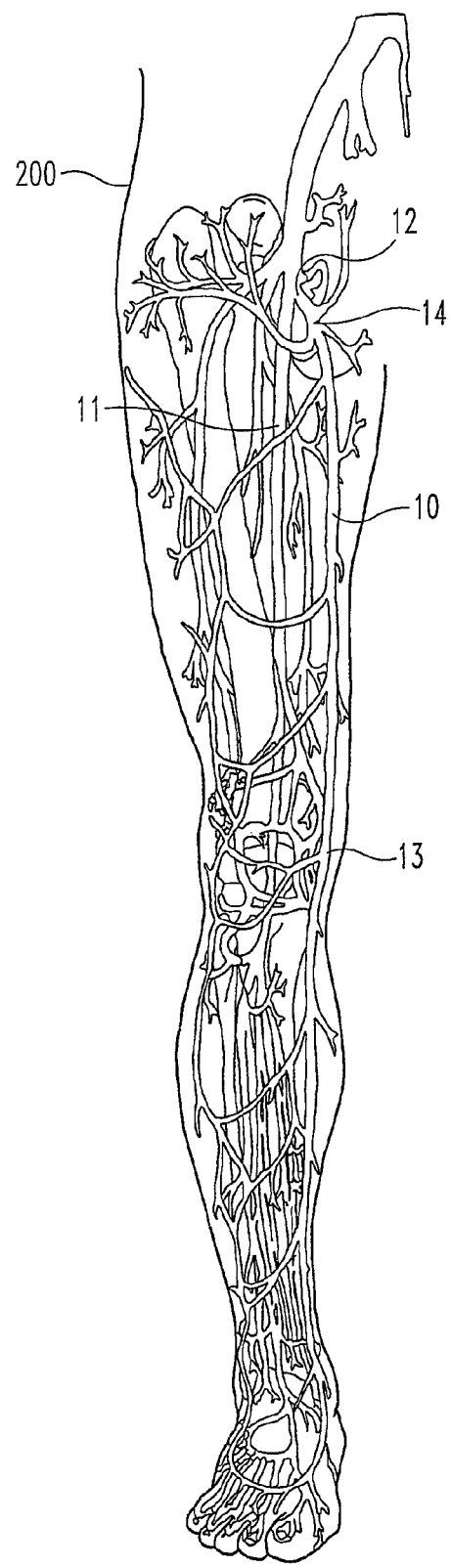
FIG. 1 depicts a human leg showing certain venous structures therein.
Figure 2:
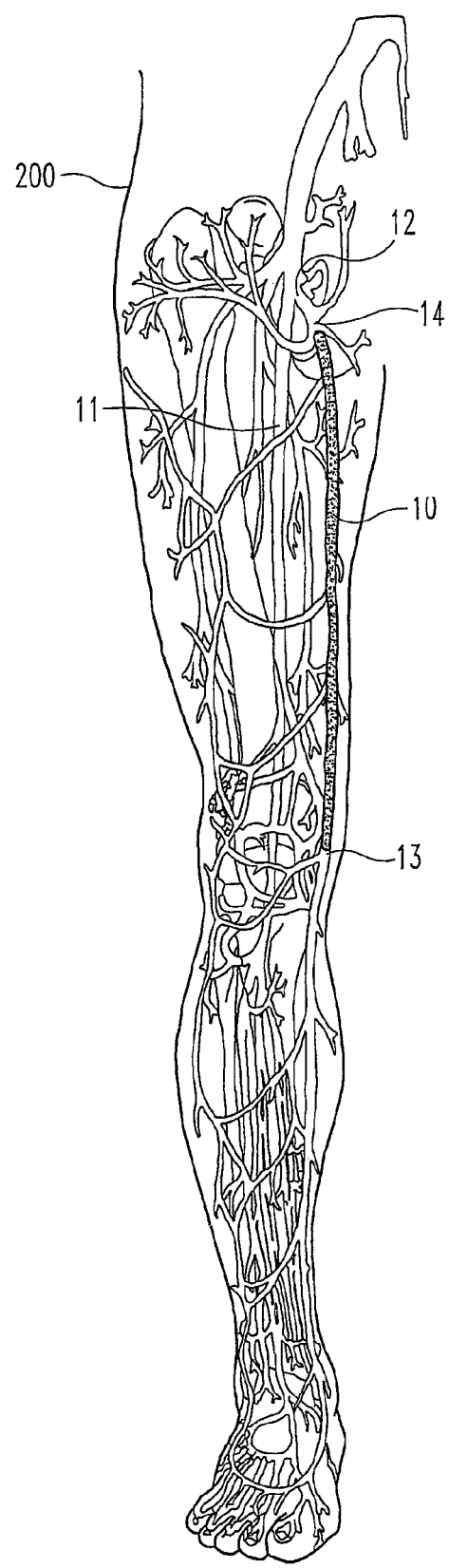
FIG. 2 depicts a human leg showing certain venous structures therein.

With reference now more particularly to the figures, shown in FIG. 1 is a diagram of a human leg 200 showing certain venous structures therein. In particular, shown is human leg 200 having GSV 10 and femoral vein 11 which adjoin at the sapheno-femoral junction 12. In accordance with certain aspects of the present invention, the GSV 10 can be occluded in a region constituting substantially all of the passage between a point 13 occurring near the medial side of the knee to a point 14 occurring prior to the sapheno-femoral junction 12, as illustrated by the shaded area in FIG. 2. Desirably, such occlusion is effective to prevent reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
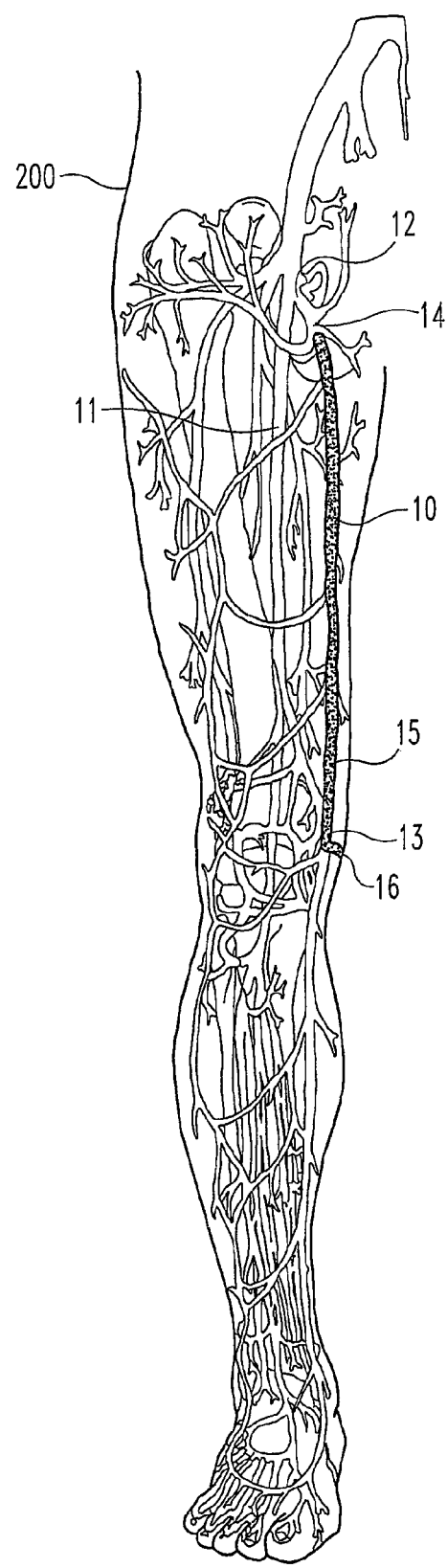
FIG. 3 depicts an illustrative embodiment of a human leg having an occlusion device located in the greater saphenous vein.

With reference now to FIG. 3, in certain forms of the invention, occlusion of the passage of the greater saphenous vein occurring between points 13 and 14 is achieved by an elongate occlusion device 15 that extends from point 13 to point 14, and that may include an end portion 16 that traverses the wall of the GSV 10. This may be achieved by deploying an occlusion device 15, such as one or more sheets or strands of material or a sponge form material, during a percutaneous procedure, e.g. as described herein. Additionally, the occlusion device 15 can comprise a remodelable material such that the patient's tissue remodels the device to enhance and promote occlusion of the GSV.

With general reference to FIGS. 4A through 8, certain deployment procedures can include the passage of a vascular occlusive device over an elongate guiding member, such as a wire guide. Alternative procedures can include the passage of an occlusive device over an endoluminal device that is advancable within the vasculature. Still alternative procedures can include the implantation of an elongate occlusive device that is advancable through the vasculature to the implant location. Such deployment procedures generally include the open or sheathless passage of the occlusion device through the vascular segment once luminal access is achieved via a percutaneously placed cannulated device, such as an introducer sheath.

Figure 4A:
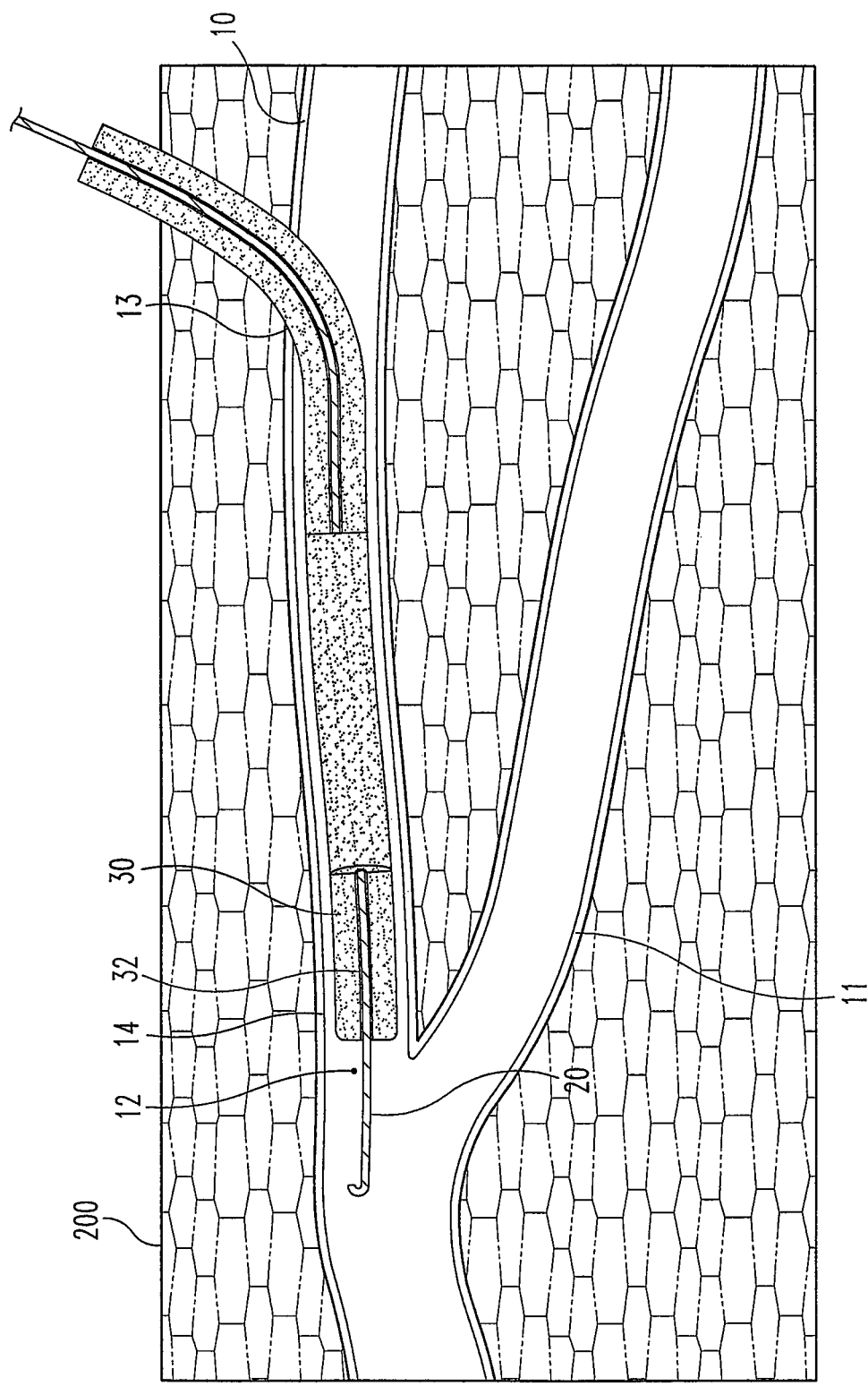
FIG. 4A depicts an illustrative deployment embodiment in that portion of the human leg occurring generally between points 13 and 14 in FIG. 1.
Figure 4B:
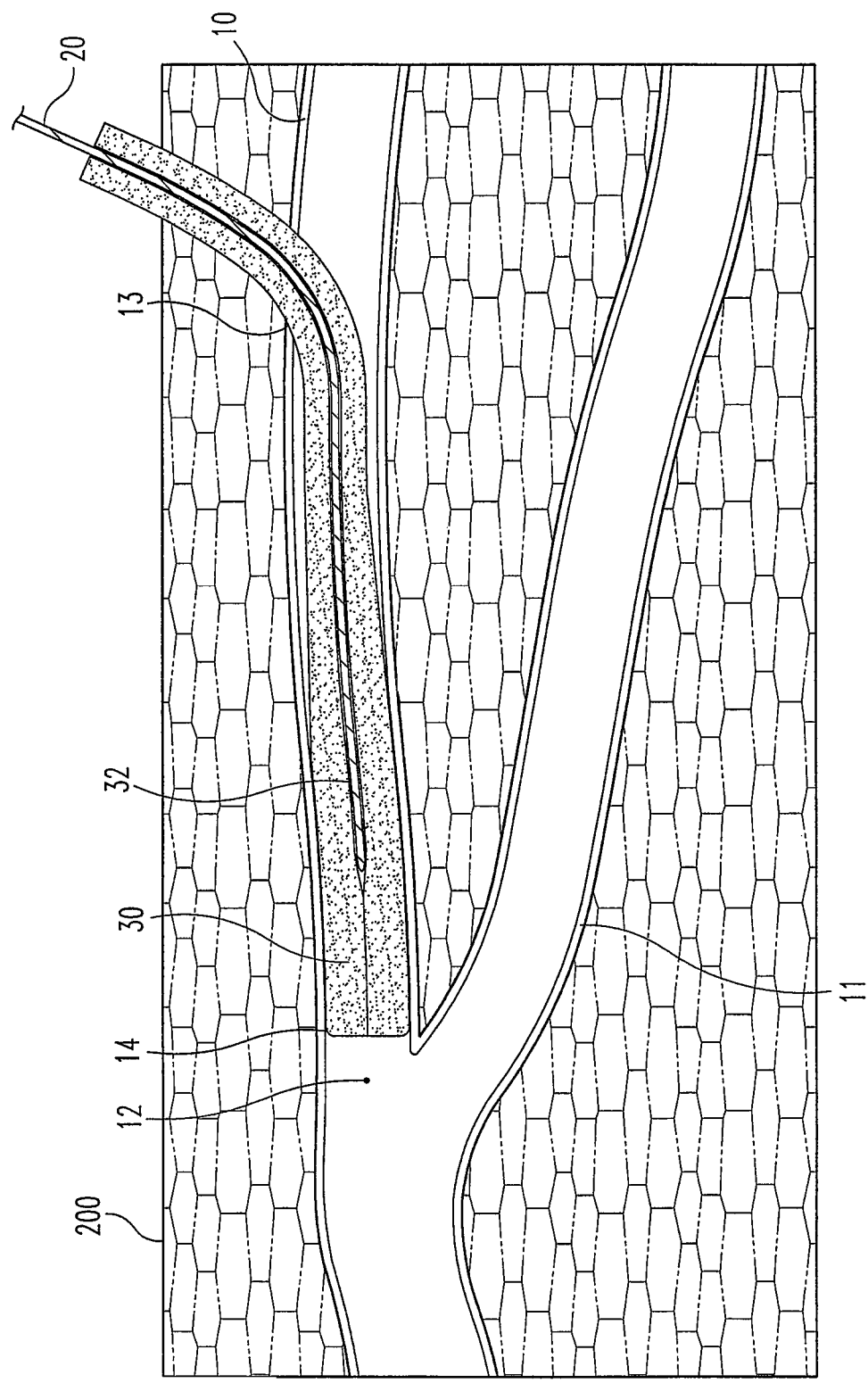
FIG. 4B depicts an illustrative deployment embodiment in that portion of the human leg occurring generally between points 13 and 14 in FIG. 1.
Figure 4C:
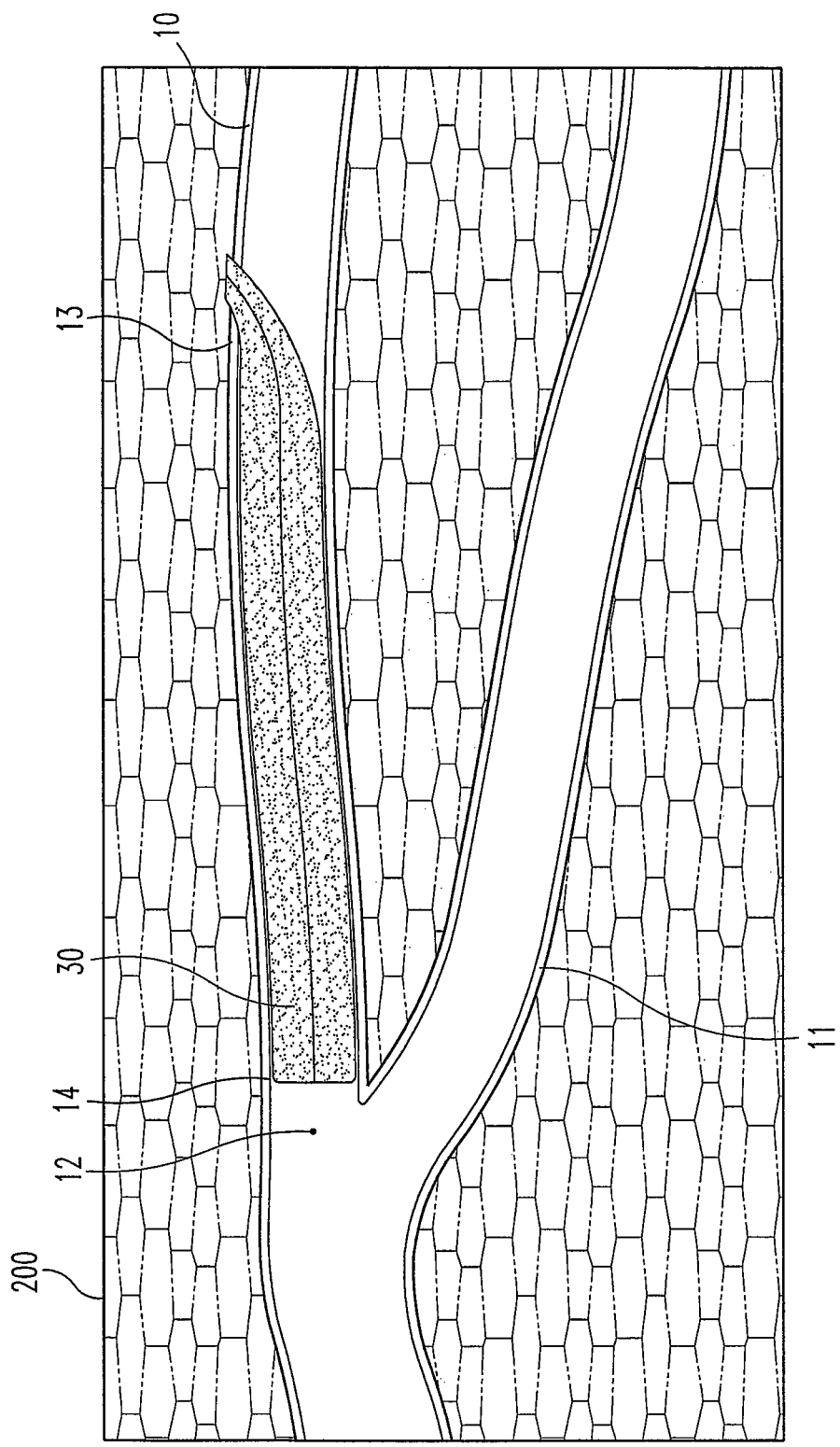
FIG. 4C depicts an illustrative deployment embodiment in that portion of the human leg occurring generally between points 13 and 14 in FIG. 1.

Turning more specifically now to FIGS. 4A through 4C, shown is an enlarged view of that portion of the human leg occurring generally between points 13 and 14 of FIG. 1. In an illustrative deployment procedure, percutaneous access to the GSV 10 can be achieved at point 13 using the Seldinger or any other suitable technique. For instance, an access needle (not shown) can be passed through the skin to access the GSV 10, and an elongate guiding member 20, such as a J wire guide, can be passed through the access needle and into the vein 10. Prior to the delivery of an occlusion device 30, wire guide 20 can be used for any number of conventional procedures including catheterization and imaging procedures to locate the sapheno-femoral junction 12 or other dilation procedures to open or otherwise straighten the GSV. After any such procedures that are performed, the wire guide 20 can be used to assist the delivery and deployment of an expandable sponge form occlusion device 30 within the GSV.

With reference still to FIG. 4A, the occlusion device 30 can include an aperture 32 that extends longitudinally through the core of the sponge or foam device 30 for slidably receiving the wire guide 20. After the wire guide 20 is placed within the GSV, the occluder 30 can be moved distally along the wire guide 20 until it is sufficiently positioned between points 13 and 14 within the GSV 10. In certain embodiments, the occluder 30 and wire guide 20 can be packaged in a coaxial arrangement, such as where the occluder 30 is received on a proximal portion of the wire guide for example, or in alternative embodiments, the occluder 30 can be placed or threaded over the wire guide 20 either before or after the wire guide is located within the vascular vessel.

As shown in FIG. 4B, the sponge form device 30 will expand within the GSV 10. This expansion can be facilitated by the addition of saline or other suitable fluid, e.g. patient blood, either before, during, or after emplacement of the device 30 occurs. The wire guide 20 can be removed before or during the expansion of the occluder 30 within the GSV. For example, in certain embodiments, the wire guide can be removed after a portion, such as the distal end, of the occluder 30 has become anchored within the vessel 10, e.g. through expansion and/or other anchoring techniques discussed herein. In alternative embodiments, however, the wire guide 20 can be removed before anchoring occurs and the position of the occluder 30 can be maintained such as by holding the occluder at an extracutaneous location, and/or by anchoring the occluder at a subcutaneous or other location.

With reference to FIGS. 4B and 4C, once the wire guide 20 is removed, the occluder 30 can fully expand within the GSV 10, thereby closing the aperture 32 and any void space between the occlusion device and the vessel wall. As shown in FIG. 4C, the proximal occluder end can be trimmed and secured at a subcutaneous location using one or more sutures, staples, or the like, if desirable. In alternative embodiments, the occluder can be trimmed to an intraluminal location thereby allowing the vessel wall to close, or can alternatively be anchored at an extracutaneous location, such as using one or more sutures, if desirable. Illustratively, one or more securement devices (not shown), such as anchors or barbs, can be incorporated within the occlusive device 30 so as to mitigate migration of the device within the vasculature.

Figure 5:
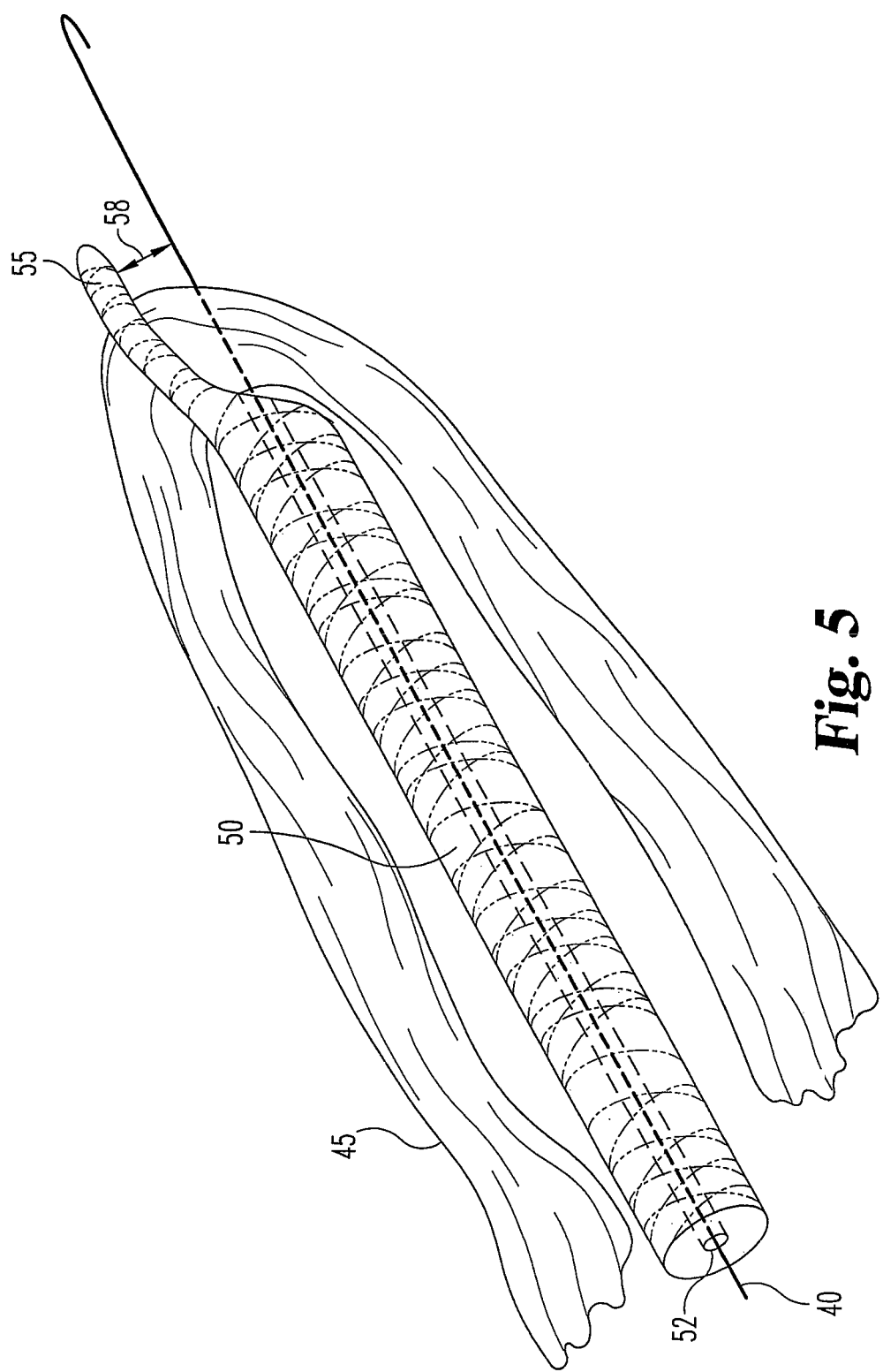
FIG. 5 depicts an illustrative method and device for occluding a bodily vessel.
Figure 6:
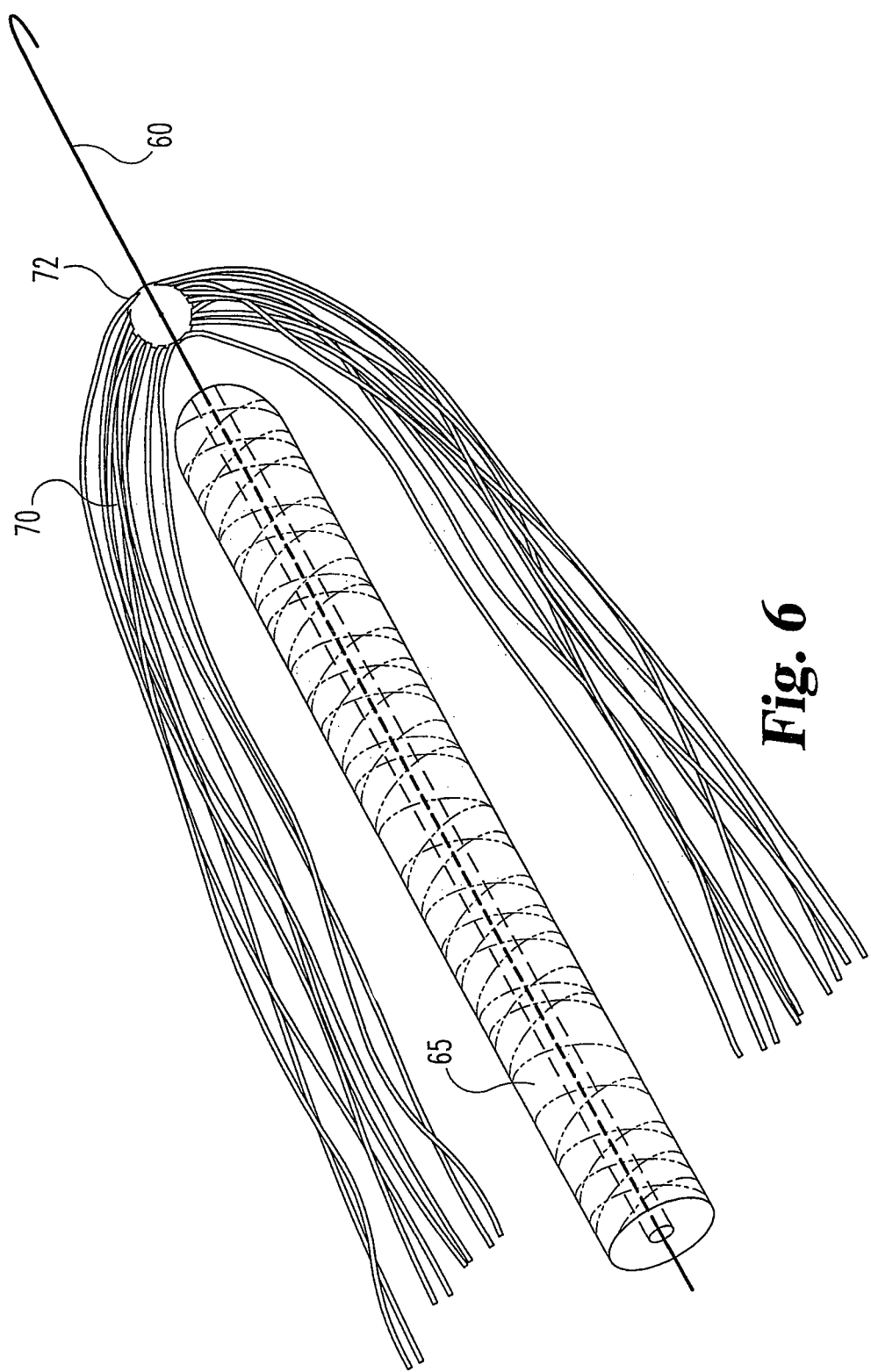
FIG. 6 depicts an illustrative method and device for occluding a bodily vessel.

With reference now to FIGS. 5 and 6, depicted are certain procedures for the low profile delivery and deployment of occluders using endoluminal devices that are guidable through the vasculature over a wire guide. With specific reference now to FIG. 5, as is depicted, an illustrative pusher 50 can have a distal adaptation, such as a protuberance 55, for contacting an occlusive device 45 during a deployment procedure. The pusher 50 can include a longitudinal aperture 52 for slidably receiving a wire guide 40, such as a J wire guide having an atraumatic end. Illustratively, the protuberance 55 can comprise an extension or projection of an outer portion of the distal most circumference of the pusher 50. In certain embodiments, the adaptation can be radially projected in an outward direction from the circumference of the pusher 50, while in alternative embodiments, the adaptation can comprise a linear extension of the outer circumference, or comprise any suitable shape or structure that is capable of releasably retaining an occlusive device during a deployment procedure. As is shown, the adaptation 55 can occupy an atraumatic shape for facilitating advancement through a bodily vessel.

With reference still to FIG. 5, the protuberance 55 and received wire guide 40 can form a pocket 58 for releasably retaining an occlusive device 45, such as one or more strands of remodelable sheet material as discussed below. In certain embodiments, a portion or fold of the occlusive device 45 can be retained within the pocket 58 while the body of the device is draped along or around the body of the endoluminal device 50. In alternative embodiments, however, such as when a wire guide is not used in the deployment procedure, the occlusion device 45, e.g. an end, can be retained on the protuberance 55 by draping or otherwise snagging or grasping a portion of the occluder 45 over the tip of the protuberance. The pocket 58 or protuberance 55 can serve to retain or contact the occlusion device 45 during delivery of the prosthesis 45 within a bodily vessel, yet provide for the ready release of the occluder 45 once the wire guide 40 and endoluminal device 50 are successively or simultaneously withdrawn from the vessel.

In illustrative embodiments, the occlusion device 45 can be of sufficient length such that the proximal end of the device 45 extends to an extracutaneous location when the fold or distal device end is located at the distal most portion of the implantation site. The occlusion device can be anchored within the patient, such as by placing one or more sutures throughout the length and/or at one or both ends of the implanted device. In additional embodiments, the occlusion device can include an anchoring device, as discussed herein, at any suitable location along the body of the device to reduce the risk of device migration after deployment occurs.

Turning now to FIG. 6, as shown, an occlusion device 70 can include a number of strands of sheet material, such as multilaminate sheets of extracellular matrix (ECM) material, interconnected at their respective distal ends by a biocompatible ring 72. The ring 72 and occlusive strands can be received over a wire guide 60 and can be moveable within a bodily lumen along the wire guide by an endoluminal device 65, such as a pusher having an atraumatic, e.g. rounded, distal end. Illustratively, the ring 72 can serve many purposes, such as connecting one or more occlusive strands together, assisting with the movement of the occlusive device through a vessel, and/or serving as an anchoring means once the occlusion device is placed within the vessel, e.g. in embodiments where the ring is made from shape memory material as is discussed herein. In alternative embodiments, the occlusion device can be delivered within the vasculature by receiving the ring over a distal protuberance of an endoluminal device, such as that depicted in FIG. 5.

Figure 7:
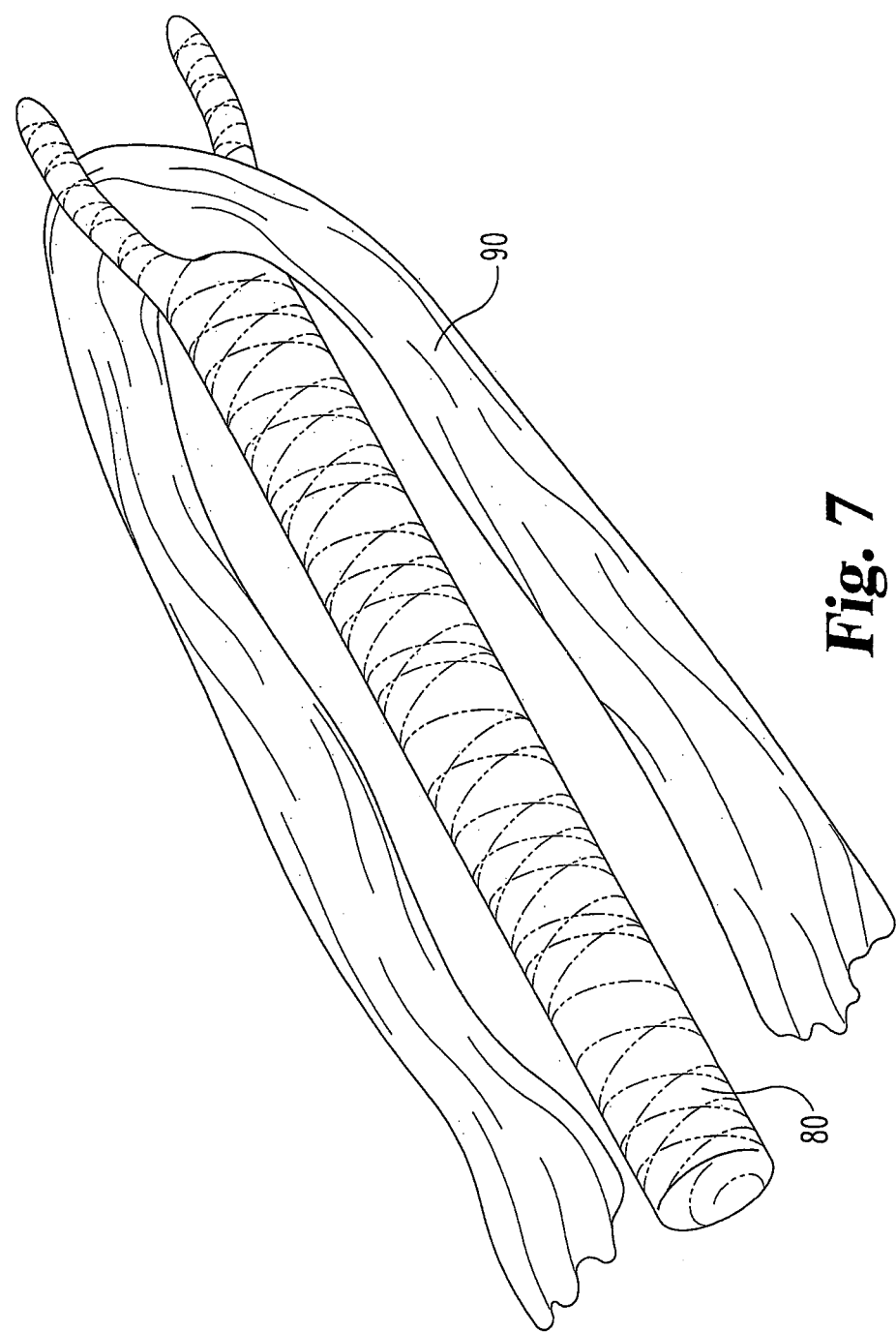
FIG. 7 depicts an illustrative method and device for occluding a bodily vessel.

Turning now to FIG. 7, an illustrative delivery system can include an endoluminal device 80 that is guidable or advancable through a bodily vessel to deploy an occlusive prosthesis 90. In certain embodiments, venous access can be facilitated using a short introducer sheath, which can optionally be removed after the endoluminal device and occluder are placed within the vein. The endoluminal device 80 can include an adaptation that forms a fork-like shape at the distal end of the device for releasably holding or grasping the occlusion device 90. The endoluminal device 80 can be maneuverable such that it is self-guidable through a bodily vessel when pushed from an extracutaneous location.

In certain embodiments, the occluder 90 can include an anchor (not shown), such as a self expanding stent, that is secured to the occluder at the distal fold. The stent can be constrained within the fork of the pusher 80 allowing the pusher and occluder to be routed through a bodily vessel. Once at the deployment site, the stent can be deployed from its constrained position to an expanded position within the vessel using any suitable technique, such as by dislodging the stent from the fork with a second endoluminal device, and/or by pulling the stent from the fork by sliding the occlusion material through the device (such as by moving one end of the occlusive material in a proximal direction), and/or by twisting the endoluminal device or using other mechanical means to release the stent.

Figure 8:
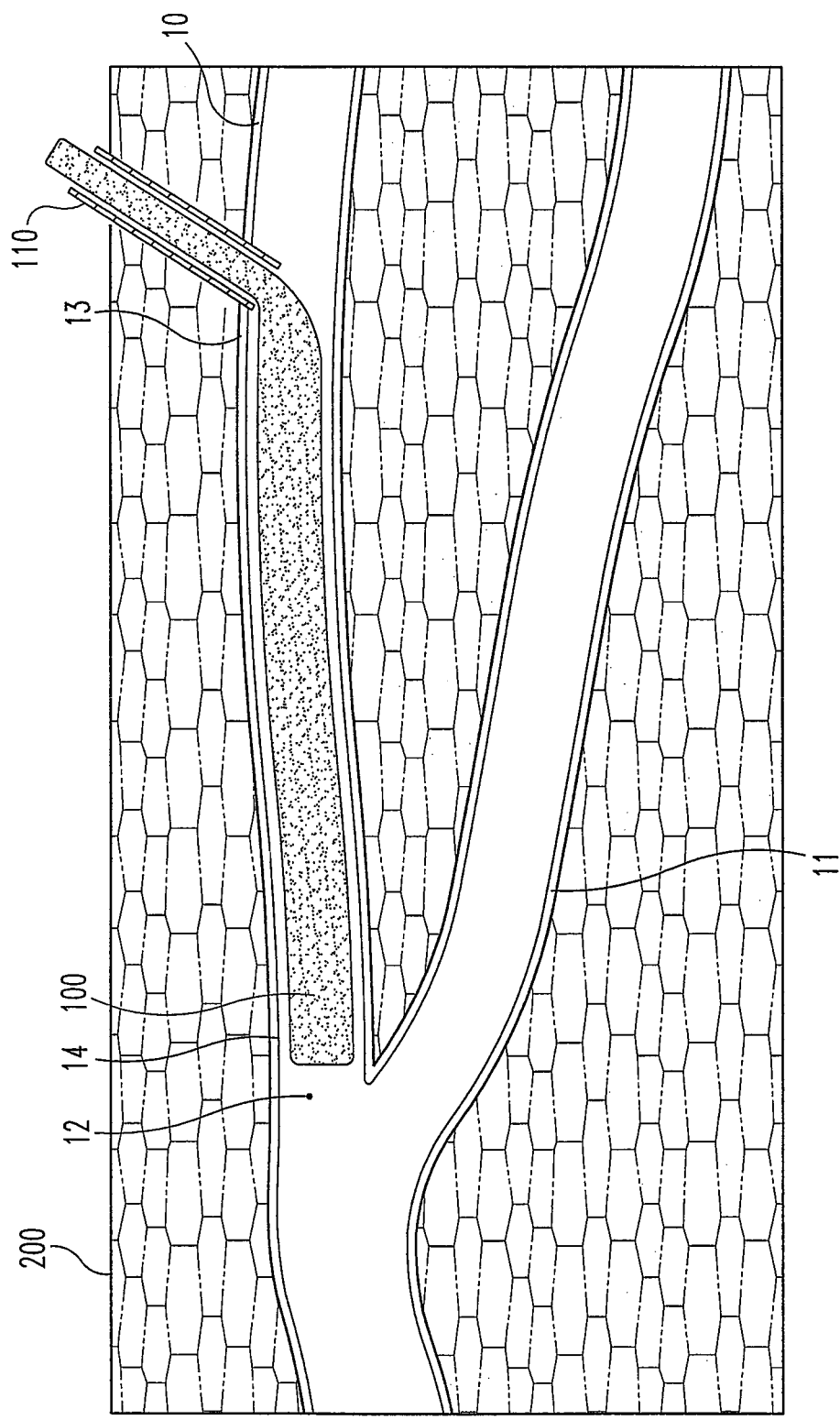
FIG. 8 depicts an illustrative deployment embodiment in that portion of the human leg occurring generally between points 13 and 14 in FIG. 1.

With reference now to FIG. 8, an implantable occlusion device 100 can be advanced through a venous vessel 10 by pushing the device in a distal direction from an extracutaneous location. Illustrative such advancable devices can include any suitable occlusive device that has sufficient column strength or pushability for advancement through a bodily vessel, e.g. an expandable foam device or layered construct as discussed herein. In certain embodiments, an introduction device 110, such as a peel away sheath can be used to provide a readily accessible path for entry of the device 100 into the vessel 10. Additionally, a dilator or other suitable device can be passed through the vein 10 to straighten and/or open the vessel 10 before advancement of the occlusion device occurs, if desirable.

Figure 9:
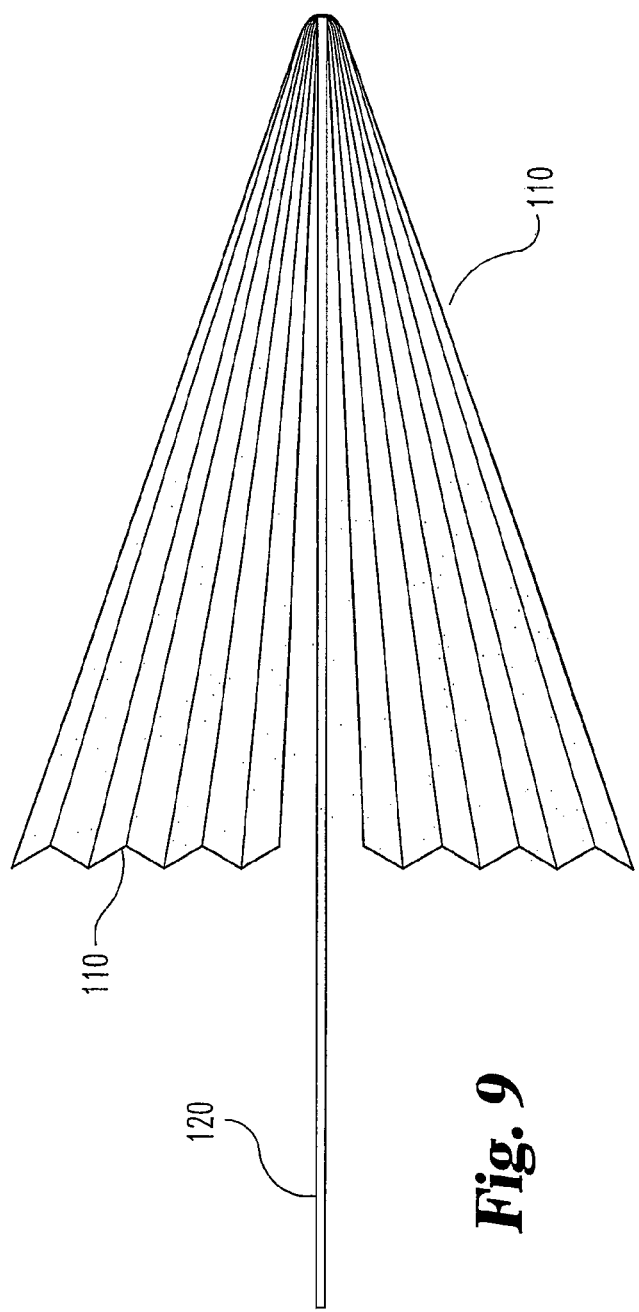
FIG. 9 depicts an illustrative device for occluding a bodily vessel.

Turning now to FIG. 9, depicted is an illustrative medical device that includes a single layered sheet of lyophilized small intestine submucosa 110, which has been fan-folded and wrapped around the distal end of a pushing device 120 for sheathless delivery within a vascular vessel of interest. The pre-fan-folded sheet can have a width of 5 cm and a non-folded length of 60 cm. In alternative embodiments, the sheet can have a dimension of 5 cm by 40 cm, 2.5 cm by 60 cm, or any other dimension that is suitable for occluding a bodily vessel of interest. In additional embodiments, a plurality of lyophilized or other ECM sheets can be wrapped around or otherwise attached to the distal end, or anywhere along, a pusher for sheathless delivery within a vessel of interest. Such sheets can occupy different dimensions, such as different widths, in order to achieve an adequate cross-sectional diameter for delivery through the vessel. Additionally, such sheets can include both single layered sheets and/or multi-layered sheets, e.g. multilaminate sheet form material, in order to vary the cross-sectional diameter of the delivery system to fit the occlusive and/or delivery need of the vessel. In certain aspects, the folded tip of sheet material can be formed into a bullet like or other suitable shape for ready receipt over the distal end of the pusher. In alternative embodiments, the illustrative pusher 120 depicted in FIG. 9 can include a longitudinal aperture for receiving a wire guide. In such embodiments, the wire guide can optionally penetrate the fold of sheet material in order to releasable retain the sheet material over the pusher during deployment.

Figure 10:
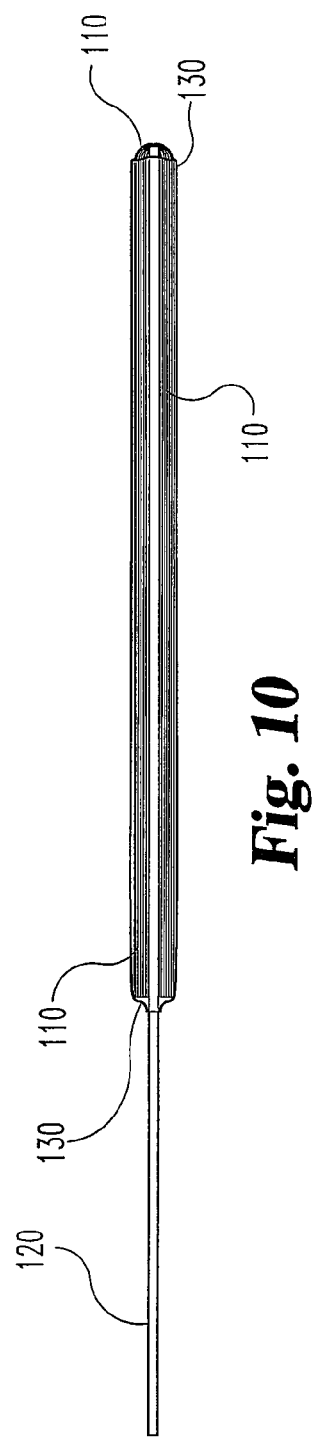
FIG. 10 depicts an illustrative device for occluding a bodily vessel.

With reference now to FIG. 10, an illustrative wrap 130 can be added to the medical device of FIG. 9 in order to enhance the pushability of the device through the vasculature. As shown, the wrap 130 can comprise a sheet of vacuum pressed small intestine submucosa, which is wrapped around the fan-folded material 110 shinny side out so as to compress the fan-folded material 110 around the pusher 120 and positively enhance the column strength of the assembly. The wrap 130 can be wound around the sheet-form material 110 one or more times as is desirable to achieve a desired assembly column strength. Additionally, the wrap can extend substantially along the length of the folded material 110, or in alternative embodiments can extend only partially or intermittently along the length of the folded material 110. The wrap 110 can comprise any suitable biocompatible material, as discussed herein, such as an ECM material and/or a synthetic material, such as fluorinated ethylene propylene. In certain embodiments, such as when the wrap includes a synthetic material, the wrap can optionally be removed from the assembly after delivery, such as by pulling the wrap in a distal direction after the folded material is sufficiently located at an implant site. For example, the wrap and pusher can be removed successively, such as a staged succession, or simultaneously from the vascular vessel in order to deploy the occlusive material within the vessel. In additional embodiments, the depicted medical device can be located within a vessel of interest after the vessel has been dilated with a dilator of sufficient size such that it somewhat straightens and somewhat opens the vessel for receipt of the occlusive device.

Occlusive devices can be anchored during illustrative deployment procedures using any suitable securement method or device. For example, one or more sutures or staples can be used to secure the device to patient tissue. Such sutures or staples can be placed at either end of the device, or along the body of the device, such as by using an endoluminal suturing device. Additionally or alternatively, the occlusion device can include one or more barbs or other anchoring devices to mitigate migration after or during implantation.

For example, an anchor can include a self expanding stent that can be attached to the occlusive material at any suitable location and that can be deployed within the vessel to secure the occluder against movement. In certain embodiments, the self-expanding stent can be attached at the proximal end of the occlusive device and can be deployed through an introducer sheath so as to expand within the vessel at a proximal location. In alternative embodiments, the self expanding stent can be attached at a more distal portion of the occlusive device and can be constrained during delivery by the endoluminal device and can be thereafter expanded within the vessel using any suitable device or technique, such as by maintaining the position of the stent with a pusher while retracting the endoluminal device and/or as discussed herein or otherwise.

In alternative embodiments, an anchor can include an expandable stent or metal. The expandable stent can be attached to the occlusive device, delivered to an implant location in a collapsed state with the occlusive device, and then expanded using suitable means to expand the stent and secure the device the within the patient. Suitable such expansion means can include the use of a percutaneously inflatable balloon or expandable coil device, or if the stent comprises a shape memory metal, the anchor can expand upon a change in temperature, such as by being raised to body temperature and/or by delivering heat to the metal using a percutaneous technique, such as delivering an electrical current to the metal.

Turning now to a discussion of occlusive device materials, illustrative such materials can include any suitable biocompatible material. Generally, the occlusion materials may include synthetic materials or reconstituted or naturally-derived collagenous materials. Such biocompatible materials that are at least bioresorbable will provide advantage in embodiments of the invention, with materials that are bioremodelable and promote cellular invasion and ingrowth providing particular advantage. Illustratively, remodelable materials may be used in this context to promote cellular growth within the occlusive materials to promote the closure of an occluded passageway.

Bioremodelable materials of the invention can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the invention will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the ECM material within the patient.

Submucosa or other ECM material used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present invention.

Turning now to a discussion of three-dimensionally stable materials that can be formed into occlusive constructs for use in aspects of the invention, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collageneous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wetability and rapid hydration and expansion of closure devices of the invention.

Preferred sources of collagen for forming sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming occlusive bodies can be highly dense, typically having densities of at least about 0.05 g/cm$^3$, preferably in the range of about 0.05 g/cm$^3$ to about 0.2 g/cm$^3$, and more preferably about 0.075 g/cm$^3$ to about 0.2 g/cm$^3$. The compacted sponge matrix can have sufficient rigidity to be deployed by passage through bodily vessels, needles, catheters or sheaths, such as by utilizing a push rod or other pusher element to force the sponge matrix body through the needle and/or catheter cannula for example. Expanded sponge densities (dry) will generally be less than the corresponding compacted densities. Typical expanded densities (dry) will range from about 0.01 g/cm$^3$ to about 0.1 g/cm$^3$, more preferably about 0.02 g/cm$^3$ to about 0.07 g/cm$^3$.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in embodiments of the invention, reference can be made, for example, to U.S. Pat. App. Pub. No. 2003/0013989.

In additional embodiments, occlusion devices of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of occlusive devices. Methods for preparing such occlusive devices can include contacting an ECM or other collagenous starting material with an alkaline substance in an amount effective to expand the material, casting or otherwise forming the expanded collagenous material into an occlusive shape (e.g. an elongate tube or cylinder), and lyophilizing the expanded material to form a dried occlusive device.

Turning now to a discussion of synthetic materials that can be used to form occlusive constructs for use in aspects of the invention, such materials can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof. Illustrative resorbable synthetic materials can include polylactic acid, polyglycolic acid or copolymers thereof, a polyanhydride, polycaprolactone, polyhydroxy-butyrate valerate, polyhydroxyalkanoate, or another biodegradable polymer or mixture thereof. For further information concerning suitable synthetic materials (both biodegradable and nonbiodegradable), useful in certain aspects of the invention, reference can be made, for example, to U.S. Utility Pat. App. No. 2005/0228486 entitled, "Implantable Frame with Variable Compliance," filed on Apr. 11, 2005.

Turning now to a discussion of materials useful in forming miscellaneous occluder components, e.g. connecting ring and/or anchors, such as stents, such materials can include any suitable biocompatible material, natural or synthetic. Illustrative materials may include, for example, metals and metal alloys such as Nitinol or other shape-memory materials, or stainless steel, as well as resorbable or nonresorbable polymeric materials, as discussed above. For further information concerning these materials, reference can be made, for example, to U.S. Utility Pat. App. No. 2005/0228486 entitled, "Implantable Frame with Variable Compliance," filed on Apr. 11, 2005.

Occlusive devices for use in aspects of the invention may include any occlusive device that is pushable or guidable through a bodily vessel or bodily lumen as discussed herein and that will close or occlude the vessel after implantation. Illustrative such devices can occupy any suitable volumetric shape, form, size, and material. Such devices can include single or multilaminate sheet material, such as in a fan folded configuration that can be delivered and deployed at an implantation site in a folded over, such as folded in half lengthwise, configuration. Additional such guidable devices can include elongate sponge form devices that can be delivered and deployed in a folded-over, such as folded in half over a deployment device, or non-folded configuration. In some forms, self-guidable devices can include an elongate foam or sponge cylinder or other member in a dried, compressed state, wherein the cylinder or other elongate member has sufficient column strength to be advanced on its own through a vein or other vascular vessel by the application of force to the trailing end region of the member. In certain embodiments, the compressed material is effective to expand when wetted with water or other fluids, e.g. blood or other bodily fluids. Alternative such self-guidable devices can include a sheet material that is processed to itself such that it provides sufficient stiffness to the material to be advancable through a vein or other bodily vessel, or a material that incorporates certain rigid or semi-rigid materials or objects that enhance the stiffness of the occlusive material to make the material guidable through a bodily lumen.

Suitable such self guidable-devices can include occlusive devices that exhibit a column strength of at least about 200 kPA, for instance between about 200 kPA and about 12,000 kPA or more. In addition embodiments, the self-guidable occlusive device has a column strength of at least about 700 kPA, for example within the range of from about 700 kPA to about 11,000 kPA. Still additional devices can have column strengths from about 1,000 kPA to about 10,000 kPA, or from about 1,000 kPA to about 3,000 kPA. Such column strength values can be measured using a conventional Instron compressive strength testing machine. A sample of occlusive material, 5 cm in length, can be secured between to two test fixtures such that 0.5 cm of material is held within in each fixture. This test assembly results in a span of 4 cm of occlusive material between each fixture face. Thereafter, the fixtured sample can be placed in the Instron testing machine and compressed at a rate of 30 mm/min until the sample buckles. The force recorded at the point of buckling is the column strength or pushability number of the occlusive material.

In certain work performed to date, three segments of a dry small intestine submucosa foam material, each having a pre-compressed diameter of 16 mm and a length of 5 cm, were compressed down to a diameter of 4 mm using a radial compression device. Thereafter the column strength of each sample was individually determined using an Instron compressive strength testing machine. Each test was performed by securing 0.5 cm of each end of each sample within a test fixture such that a span of 4 cm of compressed foam material extended between the faces of the fixtures. The fixed sample was then compressed by the Instron machine at a rate of 30 mm/min and the compressive force was recorded. The compressive force at the point each test sample buckled was recorded as the column strength or pushability number for each sample. The column strengths for the foam samples were determined to be 1488.5 kPA, 1849.6 kPA, and 1628.8 kPA, respectively.

It is possible for an occlusive material to comprise an elongate multilaminate material having increased column strength such that the material is self-advancable through a vascular vessel. To form a multilaminate material, two or more ECM segments can be stacked, or one ECM segment can be folded or rolled over itself at least one time, and then the layers can be fused or bonded together using a bonding technique, such as chemical cross-linking or vacuum pressing during dehydrating conditions.

An adhesive, glue or other bonding agent may also be used in achieving a bond between ECM layers. Suitable bonding agents may include, for example, collagen gels or pastes, gelatin, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents, including those others identified in the discussions above. Cross-linking of ECM materials can also be catalyzed by exposing the matrix to UV radiation, by treating the collagen-based matrix with enzymes such as transglutaminase and lysyl oxidase, and by photocross-linking. The combination of one or more of these with dehydration-induced bonding may also be used.

A variety of dehydration-induced bonding methods can be used to fuse ECM portions of the bioremodelable material. In one preferred embodiment, the multiple layers of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Occlusion devices will generally be of sufficient dimension to achieve occlusion of the desired stretch of vascular vessel, either alone or in combination with other similar or differing devices. In certain embodiments, the occlusion device, in implanted form, e.g. folded in half, will have a length of at least about 10 cm, and in many situations at least about 20 cm. Indeed, for preferred occlusion procedures involving a significant stretch of an artery or vein, occlusion devices having lengths greater than 30 cm will be used. Illustratively, in the occlusion of the greater saphenous vein in human adolescents or adults, occlusion devices having lengths of at least about 40 cm or 50 cm can be used.

In additional embodiments, one or more agents (see below) can be conjunctively or cooperatively emplaced within a patient with one or more occlusive devices as are discussed herein. Cooperative emplacement can include the contact of patient tissue with agents before, during, and/or after the occlusive device is implanted in the patient. Such tissue contact of agents can occur in those areas that will become or are in contact with one or more occlusive devices and/or are adjacent to or near the implant or prospective implant location. For example, the agents can be delivered into the patient through a cannulated lumen, such as before an occlusive device is implanted, or can be injected into a patient through a needle and syringe, such as after an occlusive device is implanted. In additional embodiments, the agents can be contained within or on the occlusive device, such as by being applied to an occlusive construct by a physician before implantation occurs, and/or by being doped, bonded, or otherwise contained within a dry occlusive construct, such as can be achieved by soaking a construct in one or more agents and thereafter drying and packaging the construct.

Illustrative such agents can include any substance that is capable of bringing about or inducing constriction, spasm, or closure in a bodily vessel of a patient and/or causing the de-epithelialization or inflammation (either dilative or constrictive), and/or otherwise initiating a healing response in patient tissue, such as a wall segment of a venous vessel. Such agents can include any suitable vasoconstrictive agent, sclerosive agent, thrombogenic agent, inflammatory agent, hypercoagulable agent, or any suitable combination of one or more of any of the above or other suitable agents. For example, suitable vasoconstrictive agents can include any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, polidocanol, sodium tetradecyl sulfate, e.g. SOTRADECOL®, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOLVE®, manufactured by Provensis, Ltd. of London, England, or any other suitable agent as disclosed in U.S. Pat. Nos. 5,676,962 and/or 6,572,873, for example.

While discussions above focus upon occluding the greater saphenous vein via access at the knee level, the greater saphenous vein may also be accessed at a lower level, e.g. near the ankle. During such access, any or all of the saphenous vein occurring between the ankle and the sapheno-femoral junction may be subjected to occlusion. Other veins in the leg(s) that may be involved in the varicose vein condition may also be occluded, alternatively or in addition to the greater saphenous vein. For example, the lesser saphenous vein, or varicose veins themselves, may be occluded and obliterated in accordance with the invention. Further, other veins or arteries in the leg(s) or elsewhere in the body may be occluded within the scope of the present invention.

Sheaths, dilators, endoluminal deployment devices, such as pushers, wire guides and needles used in the invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators and pushers can be made from conventional dilator/catheter/pusher type materials such as polyethylene, polyamide, polyurethane or vinyl, stainless steel, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Introducer sheaths used in the invention will have a lumen diameter sized to allow for the passage of a sufficient amount of occlusion material to occlude the artery or vein of interest. Illustratively, the inner diameter (I.D.) of the introducer sheath can range from about 4 French up to about 40 French.

As is conventional, the distal ends, or any desirable segment or portion, of the catheters, sheaths, dilators, wires or other components, such as occlusive devices, used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on occluder devices may include markers for non-invasive imaging, including imageable materials such as those discussed above as well as substances that can be applied to ECMs or other collagenous materials, e.g. substances containing tantalum, barium, iodine, or bismuth, e.g. in powder form.

Aspects of the invention also provide medical kits that can include, for example, endoluminal deployment devices enclosed within medical packaging potentially in combination with other components, such as one or more of an occlusion device, sheath, guidewire, etc. The final, packaged products are provided in a sterile condition. This may be achieved, for example, by gamma, e-beam or other irradiation techniques, ethylene oxide gas, or any other suitable sterilization technique, and the materials and other properties of the medical packaging will be selected accordingly.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for occluding a vascular vessel of a patient, comprising:

providing an occlusive device and an endoluminal delivery device having an atraumatic tip, wherein the occlusive device is releasably retained on the endoluminal delivery device, and wherein the occlusive device has a distal end, a proximal end, an exterior lateral surface between the distal end and proximal end and a material having sufficient column strength for sheathless advancement of the occlusion device through the lumen of the vascular vessel; and locating the occlusive device and the endoluminal delivery device at a target site within the lumen of a vascular vessel, the target site being spaced from a percutaneous access site in the vessel, said locating comprising inserting the occlusive device through the percutaneous access site and into the vessel and then advancing the occlusive device through the vascular vessel so as to advance the distal end of the occlusive device from a location within the vessel proximate to the percutaneous access site to said target site while at least a portion of the exterior lateral surface of the occlusive device is exposed within the vascular vessel;

after said advancing, anchoring the occlusive device in position at said target site through expansion of at least a portion of the occlusive device to a sufficient extent to make anchoring contact against a wall of the vessel and fill a lateral and longitudinal dimension along a continuous length of the vessel with the material of the occlusive device; and releasing the occlusive device in proximity to the target site so as to occlude or close the vascular vessel and block blood flow through the lumen of the vascular vessel.

2. The method of claim 1, wherein the occlusive device comprises an anchor.

3. The method of claim 2, wherein the anchor comprises a shape memory metal configured to move between a contracted position and an expanded position.

4. The method of claim 3, further comprising expanding the shape memory metal from a contracted position after locating the occlusive device.

5. The method of claim 4, wherein expanding comprises heating the shape memory metal.

6. The method of claim 5, wherein heating comprises delivering electrical current to the shape memory metal.

7. The method of claim 2, wherein releasing comprises expanding a stent.

8. The method of claim 7, wherein releasing further comprises expanding a self-expanding stent from a constrained position to an expanded position within the vascular vessel.

9. The method of claim 1, further comprising anchoring the occlusion device.

10. The method of claim 9, wherein anchoring comprises suturing the occlusion device in at least one location.

11. The method of claim 10, wherein suturing the occlusion device includes suturing the occlusion device at a distal location.

12. The method of claim 1, wherein releasing further comprises moving the endoluminal delivery device in a proximal direction.

13. The method of claim 1, wherein the occlusive device comprises one or more strips of extracellular matrix material, wherein each strip is folded in half about a horizontal axis.

14. The method of claim 13, wherein each unfolded extracellular matrix strip is at least about 100 cm in length.

15. The method of claim 1, wherein the endoluminal delivery device comprises a wire guide, wherein the occlusive device has a lumen, and wherein the wire guide is received through the lumen.

16. The method of claim 15, wherein the occlusive device is comprised of an elongate sponge body that expands upon contact with blood.

17. The method of claim 16, also comprising-withdrawing the wire guide from the lumen.

18. The method of claim 1, also comprising withdrawing the endoluminal delivery device from the vessel while a portion of the occlusive device extends to an extracutaneous location adjacent the patient.

19. The method of claim 1, wherein the occlusive device has a column strength of at least about 700 kPA.

20. The method of claim 1, wherein the occlusive device comprises a column of porous remodelable material.

21. The method of claim 20, wherein the porous remodelable material comprises collageneous extracellular matrix material.

22. The method of claim 21, wherein the collagenous extracellular matrix material includes submucosa.

23. The method of claim 20, wherein the porous remodelable material includes a sponge.

24. The method of claim 20, wherein the column of porous remodelable material has a column strength of at least about 700 kPA.

25. A method for occluding a vascular vessel of a patient, comprising:
providing an occlusive device and an endoluminal delivery device having an atraumatic tip, wherein the occlusive device is releasably retained on the endoluminal delivery device, and wherein the occlusive device has a distal end, a proximal end, an exterior lateral surface between the distal end and proximal end and a material having sufficient column strength for sheathless advancement of the occlusion device through the lumen of the vascular vessel;
locating the occlusive device and the endoluminal delivery device at a target site within the lumen of a vascular vessel, the target site being spaced from a percutaneous access site in the vessel, said locating comprising inserting the occlusive device through the percutaneous access site and into the vessel and then advancing the occlusive device through the vascular vessel so as to advance the distal end of the occlusive device from a location within the vessel proximate to the percutaneous access site to said target site while at least a portion of the exterior lateral surface of the occlusive device is exposed within the vascular vessel; and
releasing the occlusive device in proximity to the target site;
wherein said occlusive device fills a lateral and longitudinal dimension along a continuous length of the vessel with the material of the occlusive device so as to occlude or close the vascular vessel and block blood flow through the lumen of the vascular vessel.

26. The method of claim 25, wherein the occlusive device comprises an anchor.

27. The method of claim 26, wherein the anchor comprises a shape memory metal configured to move between a contracted position and an expanded position.

28. The method of claim 27, further comprising expanding the shape memory metal from a contracted position after locating the occlusive device.

29. The method of claim 28, wherein expanding comprises heating the shape memory metal.

30. The method of claim 29, wherein heating comprises delivering electrical current to the shape memory metal.

31. The method of claim 26, wherein releasing the occlusive device comprises expanding a stent.

32. The method of claim 31, wherein releasing further comprises expanding a self-expanding stent from a constrained position to an expanded position within the vascular vessel.

33. The method of claim 25, further comprising anchoring the occlusion device.

34. The method of claim 33, wherein anchoring comprises suturing the occlusion device in at least one location.

35. The method of claim 34, wherein suturing the occlusion device includes suturing the occlusion device at a distal location.

36. The method of claim 25, wherein releasing further comprises moving the endoluminal delivery device in a proximal direction.

37. The method of claim 25, wherein the occlusive device comprises one or more strips of extracellular matrix material, wherein each strip is folded in half about a horizontal axis.

38. The method of claim 37, wherein each unfolded extracellular matrix strip is at least about 100 cm in length.

39. The method of claim 25, wherein the occlusive device is an expandable sponge form occlusion device.

40. The method of claim 39, wherein the occlusive device is comprised of an elongate sponge body that expands upon contact with blood.

41. The method of claim 25, wherein the endoluminal delivery device comprises a wire guide, wherein the occlusive device has a lumen, and wherein the wire guide is received through the lumen.

42. The method of claim 41, wherein the occlusive device is comprised of an elongate sponge body that expands upon contact with blood.

43. The method of claim 42, also comprising-withdrawing the wire guide from the lumen.

44. The method of claim 25, also comprising withdrawing the endoluminal delivery device from the vessel while a portion of the occlusive device extends to an extracutaneous location adjacent the patient.

45. The method of claim 25, wherein the occlusive device has a column strength of at least about 700 kPA.

46. The method of claim 25, wherein the occlusive device comprises a column of porous remodelable material.

47. The method of claim 46, wherein the porous remodelable material comprises collageneous extracellular matrix material.

48. The method of claim 47, wherein the collagenous extracellular matrix material includes submucosa.

49. The method of claim 46, wherein the porous remodelable material includes a sponge.

50. The method of claim 46, wherein the column of porous remodelable material has a column strength of at least about 700 kPA.

\* \* \* \* \*